United States Patent [19]
Holtermann et al.

[11] Patent Number: 4,929,245
[45] Date of Patent: May 29, 1990

[54] SAFETY DEVICE FOR OSTOMY BAG COUPLING SYSTEM

[75] Inventors: Henri Holtermann, Saint-Jean-De-Luz; Claude Hamelin, Ascain, both of France

[73] Assignee: Laboratoires Biotrol, Paris Cedex, France

[21] Appl. No.: 179,629

[22] Filed: Apr. 8, 1988

[30] Foreign Application Priority Data

Apr. 10, 1987 [FR] France ................. 8705146

[51] Int. Cl.⁵ .............................................. A61F 5/44
[52] U.S. Cl. .................................................. 604/338
[58] Field of Search ................. 604/277, 332–345

[56] References Cited

U.S. PATENT DOCUMENTS

| 2,973,759 | 3/1961 | Plymale, Jr. | |
| 3,736,934 | 6/1973 | Hennessy | 604/342 |
| 4,460,363 | 7/1984 | Steer et al. | 604/342 |
| 4,610,676 | 9/1986 | Schneider et al. | 604/339 |
| 4,834,732 | 5/1989 | Steer et al. | 604/342 |

FOREIGN PATENT DOCUMENTS

| 0089138 | 9/1983 | European Pat. Off. | |
| 0163979 | 12/1985 | European Pat. Off. | |
| 0171255 | 2/1986 | European Pat. Off. | |
| 2387643 | 11/1978 | France | |
| 8503427 | 8/1985 | PCT Int'l Appl. | 604/342 |
| 1568860 | 6/1980 | United Kingdom | |
| 2121902 | 1/1984 | United Kingdom | |
| 2193098 | 2/1988 | United Kingdom | |

Primary Examiner—Jerome L. Kruter
Attorney, Agent, or Firm—Cushman, Darby & Cushman

[57] ABSTRACT

A connection assembly for a drainage appliance, one portion attaching to the body of the patient, the other portion attached to the drainage collection bag. The connection allows the easy removal of the bag yet assures an easily lockable joint including a continuous seal between the two portions when connected together. The two portions fit together and resilient snap-fit elements create an initially sealed relationship. A rotating locking ring on the body portion can be rotated to lock the snap-fit elements in a non-resilient condition and locks the two portions together while still permitting relative rotational motion therebetween. The bag portion can be easily removed when the locking ring is moved to an unlocked position, thereby releasing the snap-fit elements.

12 Claims, 4 Drawing Sheets

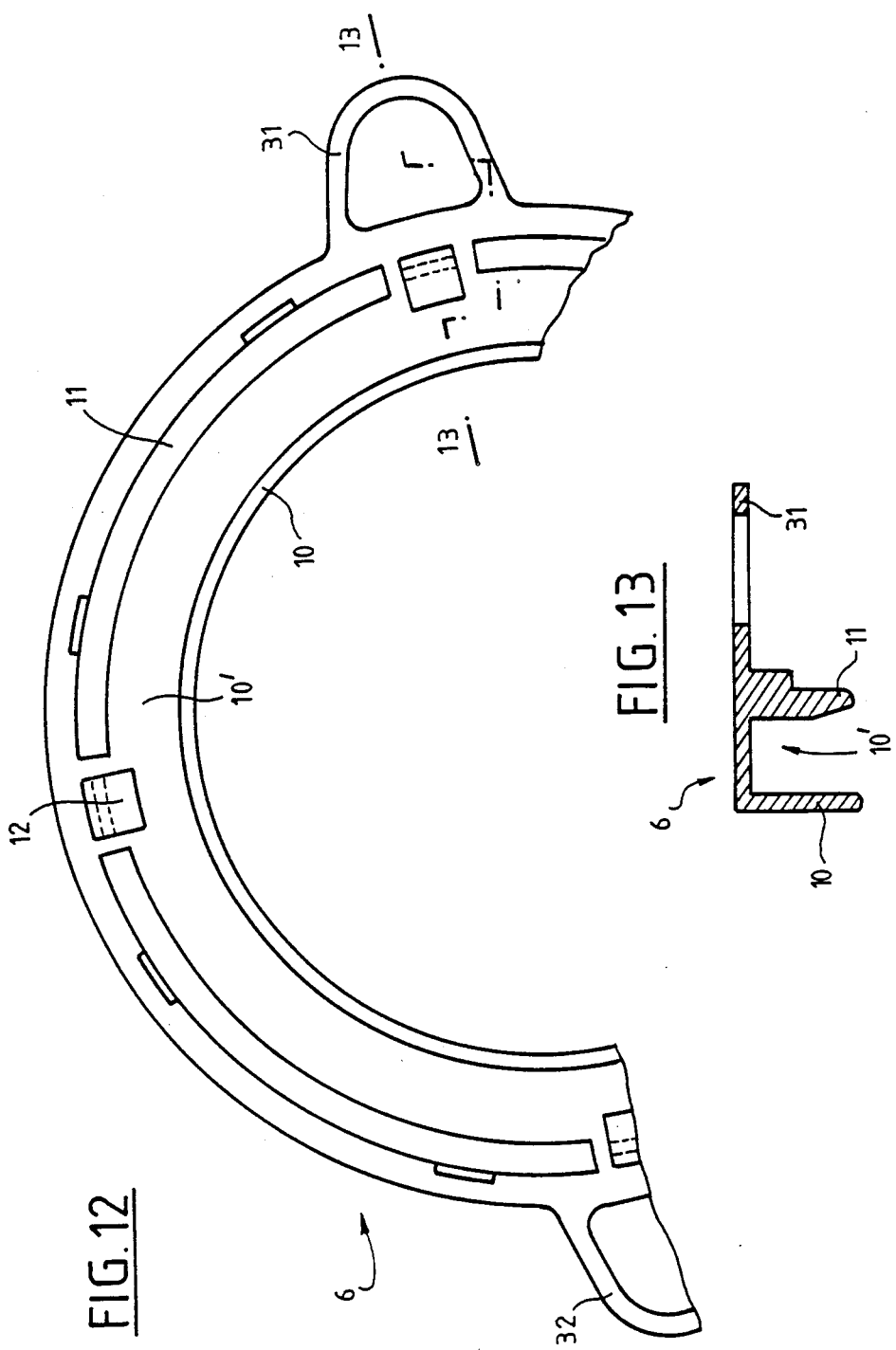

SAFETY DEVICE FOR OSTOMY BAG COUPLING SYSTEM

BACKGROUND OF THE INVENTION

1. Field of the invention

The invention relates to a safety device for an ostomy bag assembly system.

2. Description of the Prior Art

Numerous constructions are already known for assembly systems for ostomy bags, namely devices for removably fixing a bag to the user's body for collecting fluids and/or body waste evacuated by patients having undergone surgical operations on the gastrointestinal tract or the urinary apparatus, such as colostomies, ileostomies, urostomies, ureterostomies, the whole of these operations being designated hereafter under the term of ostomy. Such devices are described for example in EP-A-0 171 255 or in FR-A-2 387 643, both relating to ostomy devices with a collecting pocket in the form of a disposable bag, or which may be emptied and which is removably fixed to a ring device fixed to the user's body by means of an adhesive shoe or by a belt. The collecting bag is clipped in position by the patient who exerts a thrust or pressure about the ostomy opening so that the mating parts of the ring and of the piece integral with the bag fit sealingly together. Such devices are designed so that fixing of the bag on the ring by pressing ensures simultaneously sealing of the device, on the one hand, and, on the other, opposes an untimely separation of the bag from its mounting ring. In order to obtain satisfactory results, known devices require a considerable pressure to be exerted by the patient during assembly of the bag and the ring. Since, however, the adjacent ostomy zone is sensitive, generally painful, the application of an appreciable pressure only increases the user's discomfort so that known devices of the above mentioned type are not entirely satisfactory.

SUMMARY OF THE INVENTION

Considering the state of the Art, the primary object of the invention is to provide a safety device for an ostomy bag assembly system which is less stressful to use and in particular less unpleasant for the patient than those of known devices, while providing perfect fixing safety, not withstanding the use of a slight or very slight pressure for fixing the bag and the ring.

The present invention also provides a device which finds application whatever the method of fixing the shoe carrying the bag to the user's body wether by means of a pressure sensitive adhesive product or by means of a belt.

It is also an object of the invention to provide such a device which is applicable not only in the case of abdominal ostomy but also for ostomies of the urinary system in which a semipermanent system is sometimes used, namely a system in which the pocket or bag for collecting urine is provided with a means for discharging its contents, so that the device is not renewed at each urination but is kept by the user for a longer period than disposable devices.

It is then in such a case of use, but also for an abdominal ostomy device, an object of the invention to provide a device which allows the relative position of the bag and the ring to be slightly modified easily and without risk for the patient, even when said bag is partially filled with body fluids or waste.

The present invention provides a safety device for an ostomy bag assembly system comprising two elements one of which is provided for fixing about an artificial opening in the user's body by means of an appropriate fixing means such as a pressure sensitive adhesive means, a belt or any other similar means, and the other of which is fixed to a body fluid and/or waste collecting bag, intended to be removably fitted to said first element by snap fitting under the action of a pressure exerted when the two said elements are brought together, in which device the element associated with the shoe forming a cutaneous protector of the peristomeal zone and about the opening of one or more probes or similar which is or are fast therewith comprises, about a first tubular end-piece, a rotary member for locking—with respect to said first end-piece—a second end-piece associated with the bag and adapted to be immobilized with respect to said first end-piece when the two end-pieces are fitted together by resiliently deformable snap-fit means provided on the first end-piece and in a discrete number.

In a preferred embodiment of the invention said first tubular end-piece is formed of an internal circular ring and an external circular ring which is cut out evenly by spaces in which the snap-fit means are housed and, about which is disposed a rotary locking member, said coaxial rings defining therebetween a groove in which the second end-piece associated with a bag is adapted to snap-fit.

In a particular advantageous embodiment of the invention, said snap-fit means are formed by resiliently deformable attachment hooks spaced apart evenly from the angular point of view on the outer ring of the first end-piece and having, on the face opposite the internal ring, a nose piece which immobilizes the second end-piece when this latter cooperates with a first end-piece.

In an advantageous arrangement, the number of attachment hooks is 4, 6, 8 or 12 depending on the diameter of the end-pieces and/or the dimensions of the bags.

In a preferred embodiment of the invention, the second end-piece comprises, projecting from its external face, an annular rib with two canted faces which is housed in the groove of the first end-piece, when said two end-pieces are fitted together by causing the projections of the attachment hooks to retract.

In another preferred embodiment of the invention, the rotary locking member comprises on its internal face recesses evenly staggered from the angular point of view, whose number corresponds to that of the attachment hooks disposed on the external ring of the first end-piece and which allow said hooks to be deformed not only for fitting together but also for disassembly one from the other.

In an advantageous embodiment of the invention, the rotary locking member, knurled or not on its external surface, has a short lever facilitating the partial rotation of said member about the first end-piece.

According to another characteristic of the invention, on the external face of the external ring of the first end-piece a stud is provided for locking the rotary member which is housed, in the operating condition, in a groove with predetermined angular opening provided on the internal face of the rotary locking member, which defines the travel of the rotary locking member.

The invention also provides a body fluid and/or waste collecting bag particularly for colostomy, ileostomy, or urostomy, adapted to enter into the construction of a device such as defined above, and comprising, about an opening formed in one of its walls, an endpiece with an annular groove with two canted faces which projects from the external face of said end-piece and a resilient deformable annular lip which is situated on the internal face of said end-piece, which is integral with said wall.

The invention further provides a cutaneous protector adapted to enter in the construction of such a device, comprising, on a shoe adapted to be fixed to the user's body by means of an appropriate fixing means such, more especially, as a pressure sensitive means, a belt or any other similar means, a tubular end-piece projecting from the face of said shoe opposite that intended to come into contact with the user's body, having a coaxial internal circular ring and external circular ring, about which is disposed a rotary locking member, said rings defining therebetween a groove in which the end-piece associated with the bag is adapted to snap-fit.

Besides the above arrangements, the invention further comprises other arrangements which will be clear from the following description.

BRIEF DESCRIPTION OF THE DRAWINGS

The invention will be better understood from the following description given by way of example with reference to the accompanying drawings.

It should of course be understood that these drawings and the corresponding descriptive parts are given soley by way of illustration of the object of the invention, of which they in no wise form a limitation.

FIG. 12 is a partial view, on a larger scale, similar to FIG. 2 but for a variant, and FIG. 13 is a sectional view through line 13—13 of FIG. 12.

DESCRIPTION OF THE PREFERRED EMBODIMENT

Figure 11:
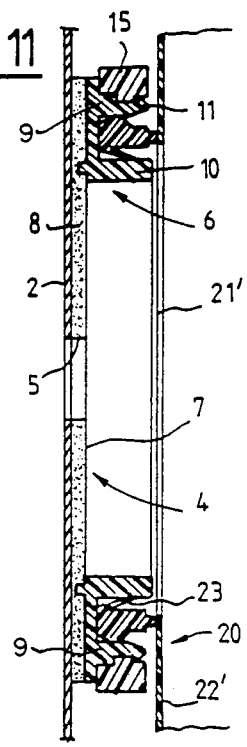
FIG. 11 is a sectional view of a device of the invention; when the two end-pieces are fitted together.

FIGS. 1 to 10 show a safety device for an ostomy bag assembly system in accordance with the invention. This device comprises an element 1, provided for fixing about an artificial opening in the user's body by means of an appropriate fixing means such as a pressure sensitive adhesive means, known per se, and which is protected, as long as the device is not used, by a film 2 which may be readily peeled away (FIG. 11), or a belt 3 or any other similar means.

Element 1 essentially comprises a shoe or pad 4 made from a flexible material, which may be of a square, rectangular, round or polygonal shape for example, intended to form a cutaneous protection for the peristomeal zone about which it is placed and held in position. This element 1 has an opening 5 concentric or substantially concentric to the stoma and an end-piece 6 projecting from the face 7 of shoe or pad 4 opposite that carrying the adhesive material 8, FIG. 11 or, when such a material is present, opposite the face in contact with the user's skin.

End piece 6 is fixed to shoe 4 by welding, for example of the thermal or high frequency type or else by bonding by means of a film compatible with the material forming end-piece 6.

Shoe 4 may be formed from a hydrophilic adhesive mass of a thickness between 0.5 and 3 mm or from a very thin acrylic adhesive mass whose thickness is between a few microns and about 200 $\mu$ or else by a combination of these two elements, mainly by providing about the stoma a hydrophilic adhesive gum and, at the periphery thereof, a thin acrylic adhesive mass.

End-piece 6 may be made from high or low density polyethylene, or from ethylene and vinyl acetate copolymer( EVA) or from polyvinyl chloride (PVC) or from a polyamide (by molding for example,) and the compatible films for fixing the end-piece on the cutaneous protector are then advantageously polyethylene, PVC, polyamide films or complex barrier films or non woven fabrics with a polyesther, polypropylene and/or polyethylene base.

End-piece 6 has a circular base 9 which carries an internal circular ring 10 and an external circular ring 11 coaxial with the first one and evenly cut out by spaces in which attachment hooks 12 are housed, said coaxial rings defining therebetween groove 10' in which the second end-piece 21 associated with bag 20 is fitted. The attachment hooks 12 have on the face, opposite the inner ring 10, a nose piece 12' (see FIG. 5) which immobilizes the second end-piece 21 fixed to the body fluid and/or waste collecting bag 20 when said collecting piece 21 cooperates with the end-piece 6 in the fitted together condition.

Figure 1:
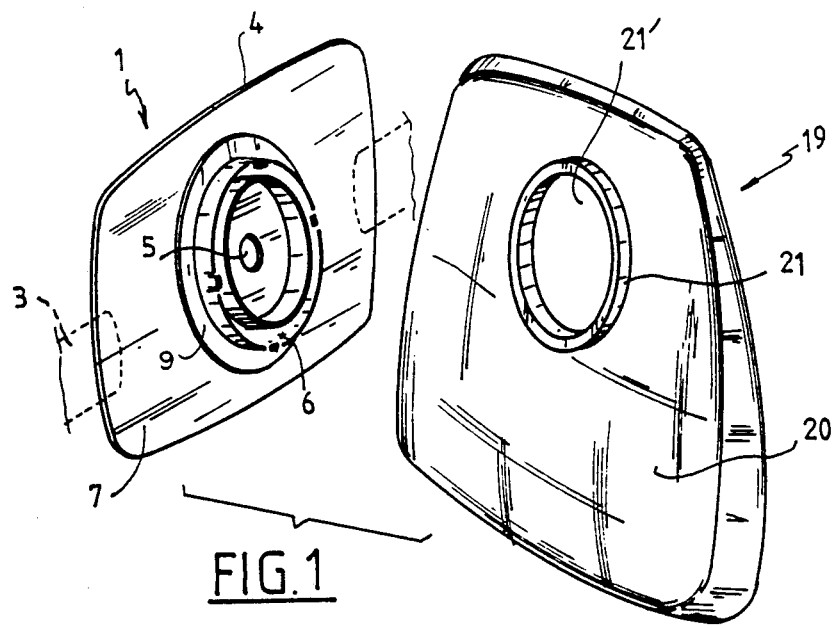
FIG. 1 is a schematical perspective view of two constituent elements of a device of the invention.
Figure 2:
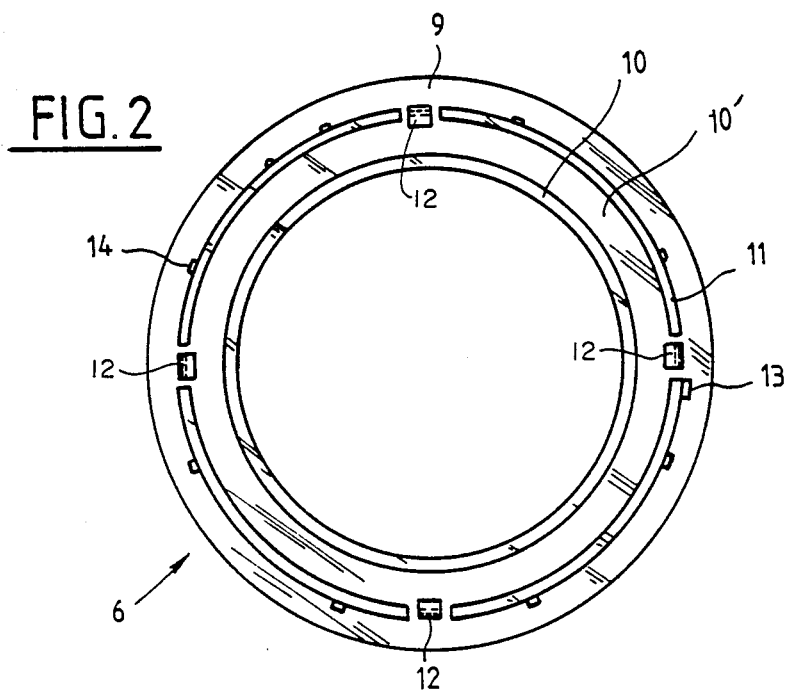
FIG. 2 is a top view of an end-piece of the device of the invention.
Figure 3:
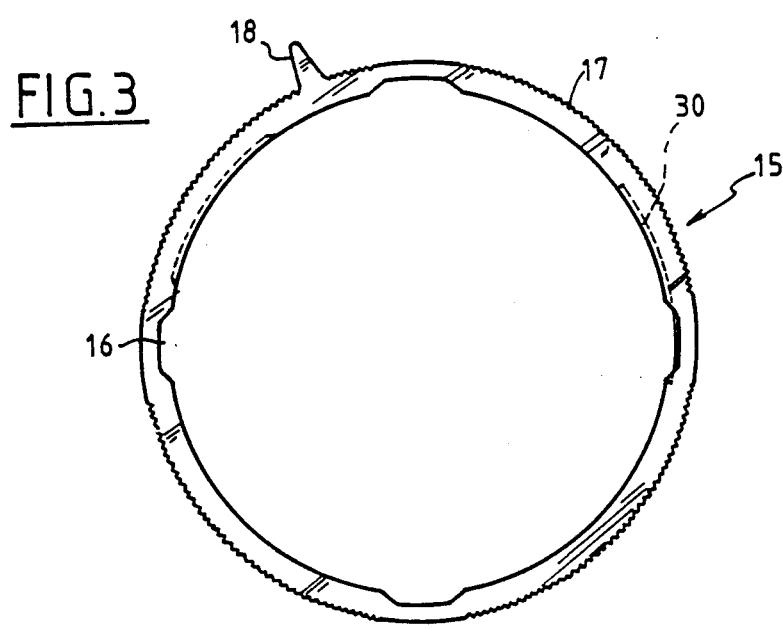
FIG. 3 is a top view of the rotary locking member of the invention.
Figure 4:
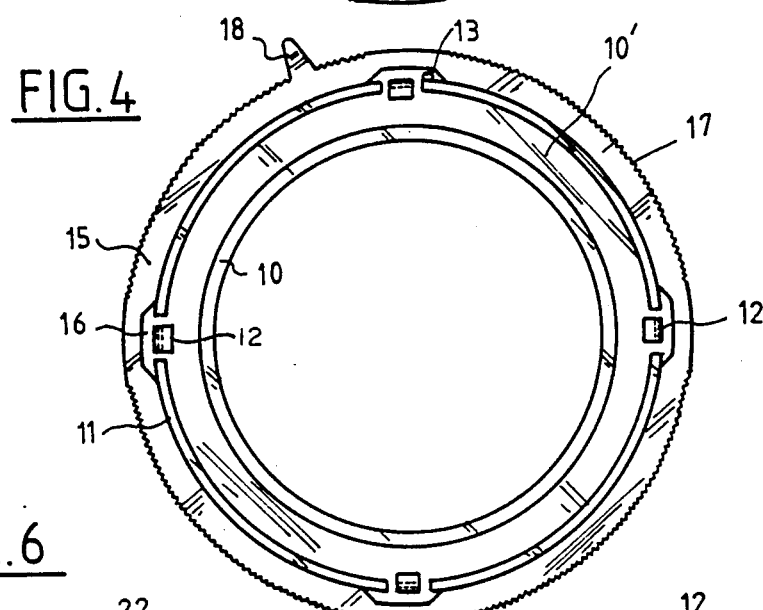
FIG. 4 is a top view of an end-piece of the device of the invention on which is disposed the rotary locking member.
Figure 6:
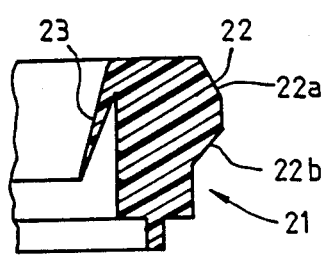
FIG. 6 is a section of the other end-piece of the device of the invention.
Figure 5:
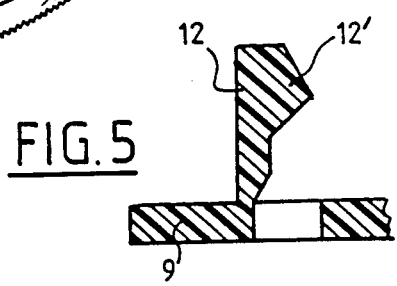
FIG. 5 is a section of an attachment hook of an end-piece of the device of the invention.
Figure 7:
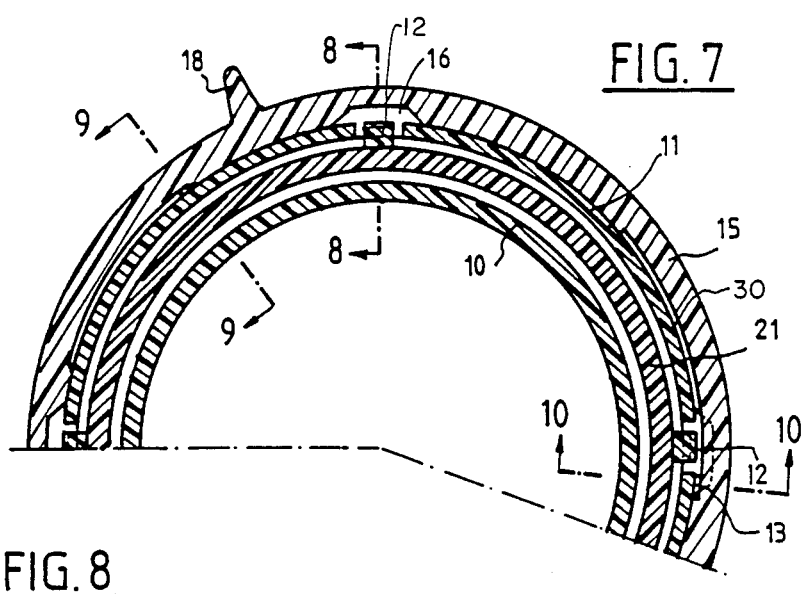
FIG. 7 is a half plane view when the two end-pieces of the device of the invention are in the fitted together condition.
Figures 8, 9, 10:
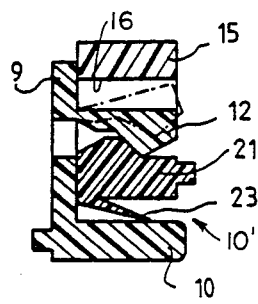
FIG. 8 is a section through line 8—8 of FIG. 7, on a larger scale.
FIG. 9 is a section through line 9—9 of FIG. 7, on a larger scale.
FIG. 10 is a section through line 10—10 of FIG. 7, on a larger scale.

The external circular ring 11 has, on the periphery of its external face, slight swellings 14 which prevent the removal of a rotary locking member 15 when this latter is disposed about ring 11, this latter also having on its external face a stud 13 for limiting the rotary movement of the rotary member 15, housed for operation in groove 30 with a predetermined angular opening, for example 45°, provided on the internal face of the rotary member 15, FIG. 3.

Said member is knurled or not on its external face 13 and has a shor&lever 18 which facilitates the partial rotation of said member about the external circular ring 11. On its internal face the rotary member 15 also has recesses 15 evenly spaced apart from the angular point of view, whose number corresponds to that of the attachment hooks 12, said recesses allowing the resilient deformation of hooks 12, when the two end-pieces 6 and 21 are fitted together and/or when they are disassembled one from the other.

The safety device for ostomy bag assembly system of the invention also comprises an element 19 adapted for removably cooperating with element 1. This element is formed essentially of bag 20 for collecting body fluids and/or waste able to be discharged through end-piece 6 and which comprises a wall 22', (FIG. 11), pierced with a hole 21' through which the body fluids or waste penetrate inside the bag, which may be of the disposable or emptyable type depending on the requirements of practice. It may be made from a polyethylene, PVC or polyamide film (such as that known under the registered trademark RILSAN) or from a complex barrier film of the polyethylene/EVA/vinylidene polychloride /EVA/ polyethylene type, such as those known under the registered trademark SAPANEX belonging to the firm DOW CHEMICAL, or a complex film of the type EVA/vinylidene polychloride-EVA copolymer, such as those known under the trademark CRYOVAC of the firm GRACE and under the registered trademark SARNEX of the firm DOW CHEMICAL, or else from a complex film of the type EVA/EVOH/EVA, or from rubber or similar.

In accordance with the invention, with bag 20 is associated the end-piece 21, advantageously made from the same plastic material as end-piece 6, for example from high density polyethylene, and is sealingly fastened to bag 20, to which it is welded or bonded, as mentioned above, so that its axis is coaxial with that of the hole 21'.

End-piece 21 has, projecting from its external face, an annular rib 22 with two canted faces 22a, 22b which is housed in groove 10', by resiliently causing the nose pieces 12' of the hcoks 12 of the first end-piece 6 to retract when the two end-pieces 6 and 21 are fitted together. End-piece 21 also has projecting from its inner face an annular deformable plastic lip 23 which, in a way known per se, seals the device against the collected fluids and/or waste.

The fact that end-piece 21 is of a mating shape and size with respect to end-piece 6 contributes to this sealing.

For positioning the device, end-piece 21 is fitted in end-piece 6 while previously making sure that the rotary locking member 15 is disposed so that recesses 16 are opposite the attachment hooks 12. During fitting together, the hooks are resiliently deformed (position shown with broken lines in FIG. 8) and penetrate into recesses 16, when the end-piece 21 is positioned at the bottom of groove 10' of end-piece 6, said hooks resume their initial position (position shower with a continuous line in FIG. 8) and hold the end-piece 21 in position in said groove 10' by means of the nose pieces 12' which are then positioned against one of the canted faces 22' of the annular groove 22 of said end-piece 21. Then the rotary member 15 is partially rotated so as to lock bag 20 with respect to shoe 4, this rotation being limited at the end of travel by abutment of the locking stud 13 on one of the edges of the groove 30 with predetermined angular opening provided on the internal face of the rotary locking member 15. With the two end-pieces 6 and 21 then fitted together and locked, rotation of element 19 with respect to element 1 is possible and the patient may take advantage of it to slightly modify the position of bag 20, even when this latter is partially filled, without separating it from shoe 4.

It is a reverse procedure which is used for separating bag 20 from shoe 4 after rotating member 15 for unlocking the hooks 12.

As is clear from the foregoing, the invention is not limited to those of its embodiments and modes of application which have been described more explicitly herein; it embraces on the contrary, all variants thereof which may occur to the mind of a technician skilled in the matter, without departing from the scope or spirit of the present invention.

Thus, and as shown in FIGS. 12 and 13, base 9 of end-piece 6 may also be provided in diametrically opposite zones with lugs 31 and 32 for attaching a belt not shown. Such a construction which also includes a shoe or pad 4 with pressure sensitive adhesive is of particular interest for patients having an invaginated stoma.

When the device of the invention is used for urostomies or ureterostomies at least one or more catheters, sounds, or the like can be attached to the shoe or pad structure, as known per se, without any modification of the other parts of the safety, device of the invention.

What is claimed is:

1. An ostomy bag system comprising a first assembly intended to be fixed about an artificial opening of a user's body by an appropriate fixing means, a second assembly including a body fluid and/or waste collecting bag intended to be removably fitted to said first assembly, said first assembly including a pad forming a cutaneous protector for the peristomeal zone, a first end-piece attached to said pad, said second assembly including a second end-piece operatively attached to the bag and adapted to interfit with said first end-piece and be immobilized with respect thereof when said first and second end-pieces are fitted together by a plurality of resiliently deformably snap-fit members provided on said first end-piece, and a rotary locking member rotatably attached to said first end-piece and rotatable between first and second positions for locking the position of said snap-fit members with respect to said second end-piece when in one of said first or second positions.

2. The device as claimed in claim 1 wherein said first end-piece is formed of an internal circular ring and an external coaxial circular ring which includes means defining a plurality of openings evenly spaced apart and within which the snap-fit members are positioned and about which is disposed said rotary locking member, said coaxial rings defining therebetween a groove in which is adapted to snap-fit said second end-piece associated with said bag.

3. The device as claimed in claim 2, wherein said snap-fit members are formed by resiliently deformable attachment hooks spaced evenly apart about the circumference of the outer ring of said first end-piece and having, on the face opposite the internal ring, a nose piece which immobilizes said second end-piece when this latter cooperates with said first end-piece.

4. The device as claimed in claim 3 wherein the number of attachment hooks can range from 4 to 12 depending on the diameter of said first and second end-pieces.

5. The device as claimed in claim 2 wherein said external ring includes an external face provided with an outwardly projecting stud, said rotary members including means defining an inwardly directed groove that extends about a predetermined portion of the circumference of said rotary member, said inwardly directed groove having a predetermined annular opening to receive said stud so that when said stud lies within annular opening rotation of said rotary member will engage said stud within said groove and lock said first and second assemblies together.

6. The device as claimed in claim 3 wherein said second end-piece is comprises of an annular rib projecting from its external face, said annular rib also including two canted faces, said annular rib being housed in the groove of said first end-piece when said first and second end-pieces are fitted together by causing the projections of the attachment hooks to retract.

7. The device as claimed in claim 3 wherein said rotary locking member includes a plurality of evenly staggered internally directed recesses whose number corresponds to the plurality of attachment hooks disposed on the external ring of said first end-piece and which allow said attachment hooks to be deformed not only for fitting together but also for disassembly one from the other.

8. The device as claimed in claim 7 wherein the rotary locking member includes an exteriorly extending lever for facilitating rotation thereof about said first end-piece.

9. The device as claimed in claim 1 wherein said first end-piece comprises a base member including hooking means for removably attaching said first assembly to a fixing belt.

10. A cutaneous protector for use with an ostomy bag assembly comprising a pad adapted to be fixed to the user's body by means of an appropriate fixing means such as a pressure sensitive means, an end-piece fixed to and projecting from the face of said pad opposite that intended to come into contact with the user's body, said end-piece having a first circular a ring and second circular ring positioned radially outwardly from and coaxial with said first ring, said first and second rings defining a groove therebetween, said second ring including means defining resiliently deformable snap-fit members adapted to engage an end-piece associated with a collecting bag and a rotary locking member rotatably mounted on said second ring and movable between locking and unlocking positions for locking the position of said snap-fit members so that such members are rendered immovable when said locking member is in its locking position.

11. A body waste collecting bag particularly for use following colostomy, ileostomy and urostomy procedures comprising means defining a waste collecting container having at least upper and lower portions, said upper portion including means defining an opening into said container including an annular member extending about the periphery thereof, said annular member including a radially extending exterior side having a first beveled surface extending therearound directed toward said opening and a second beveled surface that is directed generally downwardly away from said opening, said annular member further including an interior side having a resilient deformable annular lip positioned thereon.

12. A body waste collecting bag as in claim 11 wherein each of said beveled surfaces and said annular lip are integrally formed with said annular member.

* * * * *